United States Patent [19]

Lambert

[11] Patent Number: 4,459,317

[45] Date of Patent: Jul. 10, 1984

[54] PROCESS FOR THE PREPARATION OF A HYDROPHILIC COATING

[75] Inventor: Hans R. Lambert, Askim, Sweden

[73] Assignee: Astra Meditec Aktiebolag, Molndal, Sweden

[21] Appl. No.: 487,102

[22] Filed: Apr. 21, 1983

[30] Foreign Application Priority Data

Apr. 22, 1982 [SE] Sweden ............................ 8202524

[51] Int. Cl.$^3$ .............................................. B23B 27/06
[52] U.S. Cl. ...................................... 427/2; 428/420; 428/423.1; 428/424.6
[58] Field of Search ................. 428/420, 423.1, 424.2, 428/424.4, 424.6, 424.8; 427/2

[56] References Cited

U.S. PATENT DOCUMENTS 4,232,608 11/1980 Wrightson ........................ 428/420

FOREIGN PATENT DOCUMENTS 1600963 5/1978 United Kingdom .

Primary Examiner—Sam Silverberg
Attorney, Agent, or Firm—Brumbaugh, Graves, Donohue & Raymond

[57] ABSTRACT

A process for coating a polymer surface with a hydrophilic coating with low friction in wet condition. The process comprises applying to the polymer surface a solution containing between 0.05 to 40% of a compound which comprises at least two unreacted isocyanate groups per molecule, evaporating the solvent, applying a solution containing between 0.05 to 50% of polyethylene oxide to the thus treated polymer surface and then evaporating the solvent of the last mentioned solution, and curing the coating at elevated temperature. The process is preferably carried out in the presence of a catalyst for the curing of isocyanate.

8 Claims, No Drawings

PROCESS FOR THE PREPARATION OF A HYDROPHILIC COATING

The present invention relates to a process for coating a polymer surface with a hydrophilic coating which has a low coefficient of friction when wetted with a water based liquid, as well as medical articles being coated with a hydrophilic coating according to said process.

PRIOR ART

British Pat. No. 1,600,963 (Biosearch Medical Products Inc.) discloses a process for applying a hydrophilic coating which coating consists of an interpolymer of polyvinylpyrollidone and polyurethane, said coating having a much lower coefficient of friction in wet condition than in dry condition. Such coatings are, among other things, especially useful for medical instruments intended to be entered in body cavities, because the instrument gives a good hand grip in dry condition while simultaneously becoming very slippery when it gets in contact with body liquids or wet mucuous membranes, and thus can be inserted easily without damage to the patient. The process disclosed in said British patent has been shown to be useful for accomplishing such coatings, but is on the other hand too complicated for being suitable for large-scale production. The process described in Example 1 in the patent thus comprises not less than ten steps, whereby one of the steps takes 6 hours to carry through. A further disadvantage with this known process is that cracks are often formed in the coating.

DISCLOSURE OF THE INVENTION

The object of the invention is to provide a process for the preparation of a hydrophilic coating that has a much lower coefficient of friction in wet condition and which process is more simple and more rapid to carry out than the process disclosed in the above-mentioned British Pat. No. 1,600,963. Further the process also gives a coating that is free from cracks. These objects of the invention have surprisingly been achieved by applying a solution containing between 0.05–40% (weight/volume, that is kg/liter) of a compound containing at least two unreacted isocyanate groups per molecule to a polymer surface, evaporating the solvent, applying a solution of polyethylene oxide containing between 0.5 to 50% (weight/volume) to the thus treated polymer surface and then evaporating the solvent of the last mentioned solution, and curing the coating at elevated temperature.

The invention is explained in detail in the following.

The process according to the invention can be used for coating many different types of polymer surfaces, such as latex rubber, other rubbers, polyvinylchloride, other vinyl polymers, polyurethanes, polyesters and polyacrylates. The process has been found to be especially useful for latex, polyvinylchloride and polyurethanes.

The process according to the invention comprises applying to a polymer surface a compound containing at least two unreacted isocyanate groups per molecular dissolved in a solvent, by dipping, spraying or the like and then evaporating the solvent preferably by air drying. This step forms a coating with unreacted isocyanate groups on the polymer surface. Examples of isocyanate containing compounds that may be used are polyisocyanates such as polymethylene polyphenyl isocyanates, 4,4'-diphenylmethane diisocyanate, and 2,4-toluene diisocyanate. Prepolymers or other addition products of isocyanates and polyols are especially useful, for example prepolymers between toluene diisocyanate, or hexamethylene diisocyanate, and trimethylolpropane, or trimerized hexamethylene diisocyanate biuret. Such prepolymers are commercially available under the trade name Desmodur (Bayer AG).

The solvent for the isocyanate compound is preferably one that does not react with isocyanate. The preferred solvent is methylene chloride but it is also possible to use ethylacetate, acetone, chloroform, methyl ethyl ketone and ethylene dichloride, for example.

The isocyanate solution may advantageously contain between 0.5 to 10% (weight/volume) of isocyanate compound, and may preferably contain between 1 to 6% (weight/volume) of isocyanate compound. Generally, the solution need to be in contact with the surface only briefly, for example 5 to 60 seconds. In the case of coating of for example rubber latex it is desirable with a longer period, for example 1 to 100 minutes, to obtain a strong adherence. Another method to increase the adherence is to swell the polymer surface beforehand in a suitable solvent. A still further method is to choose a solvent for the isocyanate, such that the solvent in itself has the ability to swell or dissolve the polymer surface which is to be coated.

Following the evaporation of the solvent for the isocyanate from the polymer surface, the surface is coated with polyethylene oxide dissolved in a solvent, whereby a hydrophilic surface is obtained which subsequent to final curing of the isocyanate normally consists of a polyethylene oxide-polyurea interpolymer. The polyethylene oxide used should have a mean molecular weight of between $10^4$ to $10^7$, and the preferred mean molecular weight is about $10^5$. Polyethylene oxide having such a molecular weight is commercially available, for example under the trade name POLYOX ® (Union Carbide Corporation, U.S.A.). Examples of suitable solvents for polyethylene oxide that can be used are methylene chloride (preferred), ethyl acetate, acetone, chloroform, methyl ethyl ketone and ethylene dichloride. The proportion of polyethylene oxide in the solution is preferably between 0.5 to 10% (weight/volume) and most preferred between 2 to 8% (weight/volume). The polyethylene oxide in the solvent is applied by dipping, spraying or the like for a short period of time, for example during 5 to 50 seconds. After the polyethylene oxide solution has been applied to the coated surface, the solvent is evaporated preferably by air drying. The residual traces of solvent are removed at the curing of the coating which is preferably performed at a temperature of 50° to 100° C., in for example an oven, and during 5 to 30 minutes. All the other steps in the process may be preformed at ambient temperature.

The purpose of the curing, which is advantageously conducted in the presence of a water-containing gas such as ambient air, is to bind the isocyanate compounds together to the formation of a stable non-reactive network that binds the hydrophilic polyethylene oxide. The isocyanate groups reacts with water at the curing and yields an amine which rapidly reacts with other isocyanate groups to the formation of a urea cross-link.

According to the invention it has surprisingly been found possible to simultaneously reduce the low friction of the hydrophilic surface, to improve the adherence of the coating, and to shorten the necessary reaction times and curing times, by using some additives to the solution of isocyanate and/or the solution of polyethylene oxide. Such a suitable additive comprises different known catalysts for isocyanate curing. These catalysts may be dissolved in either the isocyanate solution or the polyethylene oxide solution but are preferably dissolved in the latter. Different types of amines are especially useful, for example different diamines, but also for example triethylene diamine. Preferably, an aliphatic amine is employed which is volatilizable at the drying and curing temperatures used for the coating, and which furthermore is non-toxic. Examples of suitable amines are N,N'-diethylethylendiamine, hexamethylendiamine, ethylendiamine, paradiaminobenzene, 1,3-propandiol-para-aminobenzoic acid diether, diaminobicyclo octane, and triethanolamine. The proportion of catalyst in the polyethylene oxide solution is suitably between 0.1 to 50% by weight of the amount of polyethylene oxide, preferably between 0.1 to 10% by weight. Some of the above-mentioned amines, particularly the diamines, can also react with isocyanate and thereby contribute to the cross-linking of the isocyanate compounds that give the desired strong adherence between the hydrophilic coating and the polymer surface.

Furthermore, it has surprisingly been shown to be possible to reduce the low friction for the hydrophilic surface still further, by way of dissolving a polymer in the isocyanate solution. Examples of suitable polymers are polyesters, polyvinyl compounds such as polyvinylchloride or polyvinylacetate, polyurethanes, polyisocyanates, or copolymers of these. These otherwise substantially inert polymers are supposed to give the surprisingly reduced friction at the surface mainly because they obstruct an undesired diffusion of not yet cross-linked isocyanate compounds out into the polyethylene oxide layer. A further reason for the low friction may be that the addition of a polymer enhance the elasticity of the coating. The proportion of dissolved polymer in the isocyanate solution is suitably between 0.5 to 20% by weight of the solution, preferably between 2 to 10% by weight.

The obtained hydrophilic coating evidently contains an appreciable amount of partly freely movable polyethylene oxide chains. Thus it has been shown that the coating can complex-bind a substantial amount of elemental iodine (compare Example 5), as is also the case with free polyethylene oxide. Such a iodine containing hydrophilic and antibacterial coating is advantageous for many medical uses, for example for urinary catheters which are intended for insertion in the urethra for extended periods of time and which otherwise is a common cause of infections. The iodine containing coating is suitably prepared by final dipping in a $KI/I_2$-solution containing at least 1% by weight of iodine, followed by drying, possibly preceeded by rinsing in a solvent.

The invention is illustrated in detail in the following Examples.

EXAMPLE 1

A pentamer of toluene diisocyanate of cyanurate type (named Desmodur IL; Bayer AG) was dissolved in methylene chloride to a concentration of 2% (weight/volume). The solution also contained a minor amount of butyl acetate. A urinary PVC catheter was dipped in this solution during 30 seconds. The catheter was allowed to dry at ambient temperature during 30 seconds, whereupon it was dipped in a solution of 6% (weight/volume) polyethylene oxide (type WSRN10; Union Carbide) in methylene chloride during 5 seconds. The catheter was then allowed to dry at ambient temperature during 60 seconds, and then during 20 minutes at 70° C. above a bowl filled with water. The catheter was finally allowed to cool to ambient temperature during 20 minutes whereupon it was rinsed in water. The catheter had a slippery and adhering surface.

EXAMPLE 2

A solution containing 0.5% (weight/volume) of the isocyanate Desmodur IL (compare Example 1) and 5% (weight/volume) of a copolymer of PVC and polyvinylacetate (20% vinylacetate/80% PVC) named LONZA CL 4520 in methylene chloride was prepared. A PVC-catheter was dipped in this solution during 15 seconds and was then dried at ambient temperature during 30 seconds, whereupon it was dipped in a solution containing 6% (weight/volume) polyethylene oxide (type WSRN10; Union Carbide; approximate mean molecular weight 100.000) and 0.23% (weight/volume) triethylendiamine in methylene chloride. The catheter was dried during 60 seconds at ambient temperature and then during 20 minutes at 70° C. above a bowl filled with water. It was then allowed to cool and was finally rinsed in water. The catheter had a slippery and adhering surface.

EXAMPLE 3

A latex catheter was swelled in methylene chloride during 30 minutes. The catheter was then dried at ambient temperature during 60 seconds, and was then dipped during 30 seconds in a solution containing 6% (weight/volume) of Desmodur L2291 (a trimerized hexamethylene diisocyanate of biuret type obtainable from Bayer AG) in methylene chloride. The catheter was dried at ambient temperature during 60 seconds and was then dipped in a solution containing 6% (weight/volume) polyethylene oxide (type WSRN10; Union Carbide) in methylene chloride. The catheter was then dried during 60 seconds at ambient temperature and finally during 20 minutes at 70° C. above a bowl filled with water.

EXAMPLE 4

The inner of a two meter long hose of PVC (inner diameter 3 mm; outer diameter 4.5 mm) was flushed with different solutions and drying agents in the following orders and periods of time:

5% (weight/volume) of Desmodur IL (compare Example 1) dissolved in methylene chloride and during 30 seconds; gaseous nitrogene of ambient temperature during 30 seconds; 2.5% (weight/volume) of polyethylene oxide (type WSRN10, Union Carbide) dissolved in methylene chloride and during 10 seconds; gaseous nitrogene of ambient temperature during 60 seconds.

The hose was then placed in an oven and gaseous nitrogene was flushed through the hose during 20 minutes. The temperature of the oven was 70° C. The nitrogene used was first bubbled through water. Finally the hose was taken out from the oven and water was flushed through the hose during 1 hour. The inside of the thus treated hose had a hydrophilic coating.

EXAMPLE 5

A urinary catheter of latex rubber was dipped during 30 seconds in a solution containing 5% (weight/volume) of Desmodur IL (compare Example 1) in methylene chloride. The catheter was then dried at ambient temperature during 60 seconds and was then dipped in a solution containing 5% (weight/volume)

polyethylene oxide (type WSRN10) in methylene chloride. The catheter was dried during 60 seconds at ambient temperature and was then cured during 20 minutes at 70° C. above a bowl of water.

After cooling the catheter it was rinsed in water and was then dipped in a saturated water solution of potassium iodide being saturated with elemental iodine. Finally the catheter was rinsed in a stream of water and was allowed to dry in ambient air. The catheter had a brown colour and chemical analysis showed that it contained iodine.

I claim:

1. A process for placing on a polymer surface a hydrophilic coating which has a low coefficient of friction when wetted with a water based liquid which comprises: applying to the polymer surface a solution containing between 0.05 to 40% (weight to volume) of a compound which comprises at least two unreacted isocyanate groups per molecule, evaporating the solvent, applying a solution containing between 0.5 to 50% (weight to volume) of polyethylene oxide having a mean molecular weight of between $10^4$ to $10^{-7}$ to the thus treated polymer surface and then evaporating the solvent of the second solution, and curing the coating at elevated temperature.

2. A process according to claim 1 wherein the solution of polyethylene oxide or the solution of isocyanate contains a catalyst that accelerates the curing of the isocyanate.

3. A process according to claim 2 wherein the catalyst comprises an amine.

4. A process according to claims 1, 2 or 3 wherein the isocyanate solution contains a polymer.

5. A process according to claim 4 wherein the polymer in the isocyanate solution is selected from the group consisting of polyesters, polyvinyl compounds, polyurethanes, polyisocyanates, or copolymers thereof.

6. A process according to claim 1 wherein the curing is performed in the presence of a water-containing gas.

7. A process according to claim 1 wherein the polymer surface to be coated comprises a polymer selected from the group consisting of latex, polyvinylchloride, and polyurethane.

8. A process according to claim 1 wherein the hydrophilic coating is treated with iodine.

* * * * *

UNITED STATES PATENT AND TRADEMARK OFFICE
CERTIFICATE OF CORRECTION

PATENT NO. : 4,459,317
DATED : July 10, 1984
INVENTOR(S) : Hans R. Lambert

It is certified that error appears in the above-identified patent and that said Letters Patent is hereby corrected as shown below:

First page, 7th line of ABSTRACT, "0.05" should read --0.5--;

Col. 2, line 55, "preformed" should read --performed--;

Col. 3, line 14, "diether" should read --diesther--;

Col. 5, line 20, before "solution" insert --second--;

Add claim 9 as follows:

--9. A process according to claim 3 wherein the catalyst comprises a diamine or triethylene diamine.--

Signed and Sealed this

Twenty-seventh Day of November 1984

[SEAL]

Attest:

Attesting Officer

GERALD J. MOSSINGHOFF

Commissioner of Patents and Trademarks